US00PP12788P2

(12) United States Plant Patent
Harnett

(10) Patent No.: US PP12,788 P2
(45) Date of Patent: Jul. 23, 2002

(54) ARTEMISIA PLANT NAMED 'ORIENTAL LIMELIGHT'

(76) Inventor: Richard Frederick Harnett, Kernock Park, Pillaton, Saltash, Cornwall (GB), PL12 6R7

( * ) Notice: Subject to any disclaimer, the term of this patent is extended or adjusted under 35 U.S.C. 154(b) by 0 days.

(21) Appl. No.: 09/639,896

(22) Filed: Aug. 16, 2000

(51) Int. Cl.[7] ..... A01H 5/00

(52) U.S. Cl. ..... Plt./373
(58) Field of Search ..... Plt./373

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Artemisia plant named 'Oriental Limelight', characterized by its upright, outwardly spreading, dense and bushy growth habit; good vigor; freely basally branching plant habit; and bright yellow and green variegated leaves.

1 Drawing Sheet

BACKGROUND OF THE INVENTION

The present invention relates to a new and distinct cultivar of Artemisia plant, botanically known as *Artemisia vulgaris* and referred to by the cultivar named Oriental Limelight.

The new Artemisia is a naturally-occurring whole plant mutation of an unidentified selection of *Artemisia vulgaris*. The new Artemisia was discovered and selected by the Inventor within a population of the unidentified selection in Japan in 1991. The new Artemisia was selected based on its much brighter variegation and more uniform plant habit compared to the unidentified selection.

Asexual reproduction of the new Artemisia by terminal cuttings taken in a controlled environment in Cornwall, England, has shown that the unique features of this new Artemisia are stable and are reproduced true to type in successive generations.

SUMMARY OF THE INVENTION

The new Artemisia has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Oriental Limelight' and distinguish 'Oriental Limelight' as a new and distinct cultivar:

1. Upright, outwardly spreading, dense and bushy growth habit.
2. Good vigor.
3. Freely basally branching plant habit, plants typically do not require pinching.
4. Bright yellow and green variegated leaves.

BRIEF DESCRIPTION OF THE PHOTOGRAPHS

The accompanying colored photographs illustrate the overall appearance of the new Artemisia, showing the colors as true as it is reasonably possible to obtain in colored reproductions of this type. Colors in the photographs may differ slightly from the color values cited in the detailed botanical description which more accurately describe the actual colors of the new Artemisia.

The photograph at the top of the sheet comprises a side perspective view of three plants of 'Oriental Limelight' that were about 2 months old and grown in a 21.5-cm container.

The photograph at the bottom of the sheet comprises a close-up view of a typical terminal shoot and upper and lower surfaces of typical leaves of 'Oriental Limelight'.

DETAILED BOTANICAL DESCRIPTION

The following observations, measurements, values, and comparisons describe plants grown in Bonsall, Calif., during the late winter and early spring, under outdoor full-sun conditions with day temperatures ranging from 12 to 35° C. and night temperatures ranging from 12 to 18° C. Plants used were about 2 months old and grown in 21.5-cm containers with three plants per container. Color references are made to The Royal Horticultural Society Colour Chart except where general terms of ordinary dictionary significance are used.

Botanical classification: *Artemisia vulgaris* cultivar Oriental Limelight.

Parentage: Naturally-occurring whole plant mutation of an unidentified selection of *Artemisia vulgaris*, not patented.

Propagation:

*Type.*—By cuttings.

*Time to initiate roots.*—Summer: About 10 days at temperatures of 23° C. Winter: About 15 days at temperatures of 22° C.

*Time to develop roots.*—Summer: About 28 days at temperatures of 20° C. Winter: About 56 days at temperatures of 18° C.

*Root description.*—Fleshy, rhizomatous.

Plant description:

*General appearance.*—Herbaceous; upright and outwardly spreading; dense and bushy growth habit. Suitable for 10 to 25.5-cm containers.

*Crop time.*—To produce a 10-cm finished flowering plant from rooted cuttings, about 8 weeks are required depending on temperature and light level.

*Plant height.*—About 32 cm.

*Plant diameter or spread.*—About 27.5 cm.

*Growth rate/vigor.*—Moderate to vigorous.

*Stem description.*—Quantity of lateral branches: Freely branching; typically about 10 per plant; pinching is usually not required. Shoots also develop from rhizomes. Lateral branch length: About 10 to 40 cm. Lateral branch diameter: About 5 mm. Internode length: About 1.25 cm. Texture: Densely pubescent. Color: 148C.

*Foliage description.*—Arrangement: Alternate. Quantity: About 14 to 40 per lateral branch. Shape: Deeply dissected, typically five dissected lobes with deep sinuses. Apex: Tri-dentate. Base: Acute. Length: About 6 cm. Width: About 5.5 cm. Texture: Smooth, lower surface slightly pubescent. Fragrant: Aromatic. Petiole length: About 3.5 cm. Petiole diameter: About 2 mm. Color: Yellow and green variegated; areas of color are random and irregular in shape and size. Young leaves, upper surface: Irregular patches of 151C, 144A and 137C. Young leaves, lower surface: 147D. fully expanded leaves, upper surface: Irregular patches of 147B, 147C, 147D and 150D. Fully expanded leaves, lower surface: Irregular patches of 147and 150D. Petiole: 147C.

Flowering description: Inflorescence development has not been observed on plants of the new Artemisia.

Disease resistance: Disease resistance to pathogens common to Artemisia has not been documented.

It is claimed:

1. A new and distinct cultivar of Artemisia plant named 'Oriental Limelight', as illustrated and described.

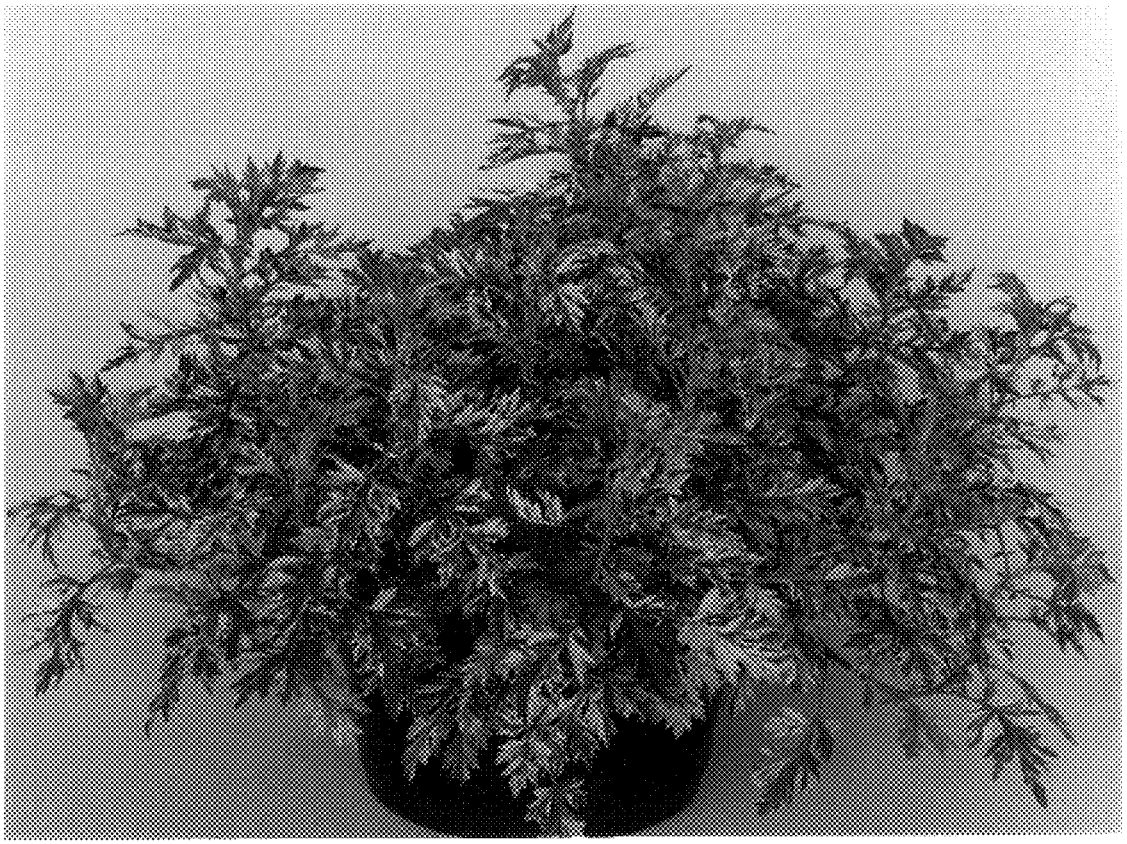
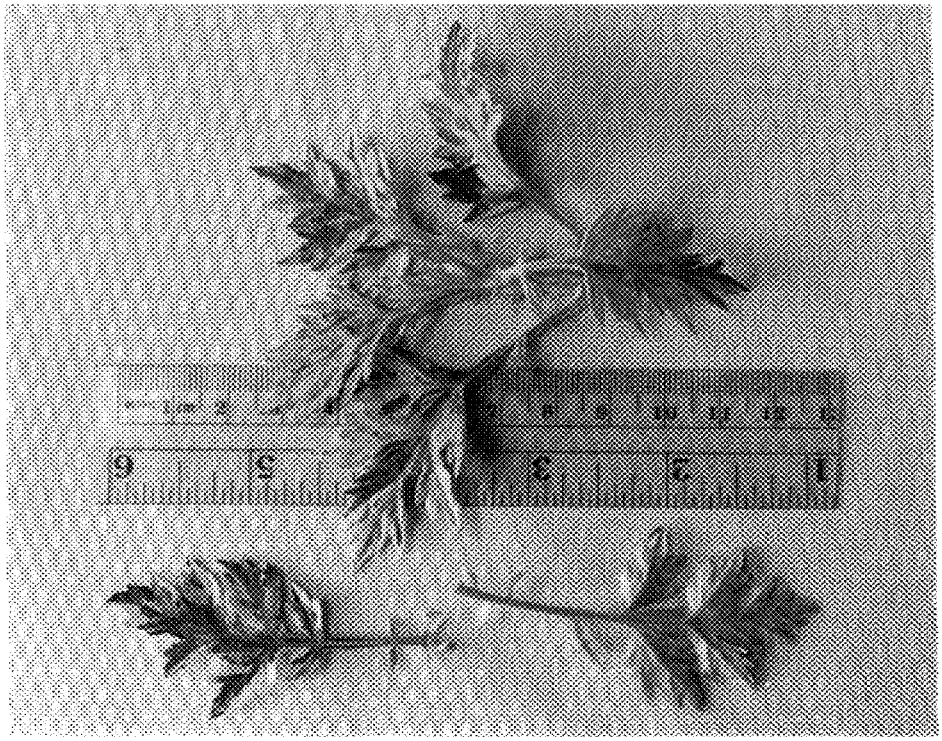

* * * * *